United States Patent [19]

McClure et al.

[11] 4,065,515

[45] Dec. 27, 1977

[54] ALKANE ISOMERIZATION PROCESS USING A SUPPORTED PERFLUORINATED POLYMER CATALYST

[75] Inventors: James D. McClure; Stanley G. Brandenberger, both of Houston, Tex.

[73] Assignee: Shell Oil Company, Houston, Tex.

[21] Appl. No.: 783,523

[22] Filed: Apr. 1, 1977

Related U.S. Application Data

[62] Division of Ser. No. 663,956, March 4, 1976, Pat. No. 4,038,213.

[51] Int. Cl.² .................................................. C07C 5/30
[52] U.S. Cl. ................................................. 260/683.68
[58] Field of Search ...................... 260/683.68, 683.65, 260/683.7, 683.75, 683.76; 252/430

[56] References Cited

U.S. PATENT DOCUMENTS

| | | | |
|---|---|---|---|
| 2,956,097 | 10/1960 | Cull et al. | 260/683.76 |
| 3,960,764 | 6/1976 | Bernard et al. | 260/683.68 |
| 4,022,847 | 5/1977 | McClure | 260/683.68 |
| 4,038,213 | 7/1977 | McClure et al. | 252/430 |

*Primary Examiner*—George J. Crasanakis
*Attorney, Agent, or Firm*—Dean F. Vance

[57] ABSTRACT

A process and catalyst for the isomerization of normal alkanes is disclosed. The catalyst is a supported solid perfluorinated polymer containing pendent sulfonic acid groups.

8 Claims, No Drawings

ALKANE ISOMERIZATION PROCESS USING A SUPPORTED PERFLUORINATED POLYMER CATALYST

CROSS-REFERENCE TO RELATED APPLICATION

This is a division of application Ser. No. 663,956, filed Mar. 4, 1976, which issued as U.S. Pat. No. 4,038,213.

BACKGROUND OF THE INVENTION

Hydrocarbon conversion and the isomerization hydrocarbons in particular, is of special importance to the petroleum industry. In recent years, with the advent of catalytic converters in automobiles and the required use of non-leaded gasoline, a need has arisen for higher octane number gasolines. Natural straight-run gasolines, i.e., naphthas, contain, chiefly, normal paraffins, such as normal pentane and normal hexane, which have relatively low octane numbers. It has become essential, therefore, to convert these low octane components to their higher octane counterparts. The isomerization of these hydrocarbon components accomplish this conversion, i.e., the isomers resulting have a much higher octane rating. Hence, the facility with which this isomerization is accomplished has become of prime importance.

Likewise, the need for isoparaffins, benzene, xylene, and ethyl benzene as building components in the petrochemical industry is increasing. Accordingly, the need for improved hydrocarbon conversion processes in the petrochemical industry is also great.

One of the primary hydrocarbon conversion processes now employed is the alkylation of isoparaffins. It was thought that certain sulfonated fluorocarbon polymers possess sufficient activity and stability to be useful as alkylation catalysts. However, in a recent study by Kapura and Gates, Sulfonated Polymers as Alkylation Catalysts, Industrial Engineering Chemistry Product Research Development, Vol. 12, No. 1, pp. 62–66 (1973), it was found that a sulfonated fluorocarbon vinyl ether polymer was inactive in alkylating isobutane with propylene in the gas phase and in a mole ratio of 5 to 1 at 260° C. The conclusion reached in that study was that the sulfonated fluorocarbon vinyl ether polymer catalyst was too weakly acidic to catalyze paraffin alkylation and that the polymer was not a useful catalyst. That study also showed that these same ion exchange resins were useful in the alkylation of benzene with propylene in the vapor phase to form cumene. However, the conclusion reached by Kapura and Gates with regard to the formation of cumene was that the sulfonated polymer was not "a particularly useful catalyst at temperatures greater than about 150° C." Contrary to the conclusions reached by Kapura and Gates, it has now been found that a supported perfluorinated polymer containing pendant sulfonic acid groups is a very active catalyst in the preparation of ethylbenzene from benzene and ethylene, in the alkylation of isoparaffins, in the isomerization of normal alkanes, and in the disproportionation of toluene.

SUMMARY OF THE INVENTION

The present invention comprises an improved hydrocarbon conversion process which comprises contacting said hydrocarbons under hydrocarbon converting conditions with a supported perfluorinated polymer catalyst containing a repeating structure selected from the group consisting of:

a) 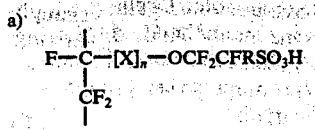

I or b) 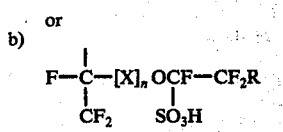

II where $n$ is 0, 1 or 2; R is a radical selected from the group consisting of fluorine and perfluoroalkyl radicals having from 1 to 10 carbon atoms; and X is selected from the group consisting of:

where $m$ is an integer from 2 to 10 and Y is a radical selected from the class consisting of fluorine and the trifluoromethyl radical.

Also disclosed is a novel catalyst composition for the conversion of hydrocarbons which comprises a catalytic component dispersed on a solid, porous support. The catalytic component is the perfluorinated polymer having the structure I or II above. The solid porous support has an effective pore diameter of between about 50 A and about 600 A and is preferably selected from the group consisting of alumina, silica, silicaalumina and porous glass.

DETAILED DESCRIPTION OF THE INVENTION

A. The Catalyst Composition

The catalyst employed in the present invention is a solid at reaction conditions. The catalyst broadly comprises a perfluorinated polymer having acid groups in the amount of about 0.01 to 5 mequiv/gram catalyst. Preferably, the polymer contains about 0.05 to 2 mequiv/gram of catalyst.

In a specific embodiment, the polymer catalyst contains a repeating structure selected from the group consisting of:

a) 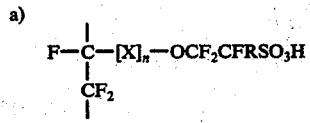

I or b) 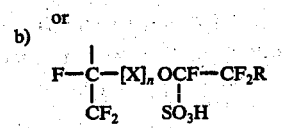

II where $n$ is 0, 1 or 2; R is a radical selected from the group consisting of fluorine and perfluoroalkyl radicals having from 1 to 10 carbon atoms; and X is selected from the group consisting of:

where $m$ is an integer from 2 to 10 and Y is a radical selected from the class consisting of fluorine and the trifluoromethyl radical. In a preferred embodiment, $n$ is 1 or 2, Y is a trifluoromethyl radical, R is fluorine, and m is 2. Catalysts of the above-noted structure typically have a molecular weight of between about 1,000 an 500,000 daltons.

Polymer catalysts of the above-noted structure can be prepared in various ways. One method, disclosed in Connolly et al, U.S. Pat. No. 3,282,875 and Cavanaugh et al, U.S. Pat. No. 3,882,093, comprises polymerizing vinyl compounds of the formula:

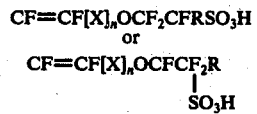

in a perfluorocarbon solvent using a perfluorinated free radical initiator. Since the vinyl ethers are liquid at reaction conditions, it is further possible to polymerize and copolymerize the vinyl ethers in bulk without the use of a solvent. Polymerization temperatures vary from −50° to +200° C depending on the initiator used. Pressure is not critical and is generally employed to control the ratio of the gaseous comonomer to the fluorocarbon vinyl ether. Suitable fluorocarbon solvents are known in the art and are generally perfluoroalkanes or perfluorocycloalkanes, such as perfluoroheptane or perfluorodimethylcyclobutane. Similarly, perfluorinated initiators are known in the art and include perfluoroperoxides and nitrogen fluorides. It is also possible to polymerize the vinyl ethers of structure III or IV in an aqueous medium using a peroxide or a redox initiator. The polymerization methods employed correspond to those established in the art for the polymerization of tetrafluoroethylene in aqueous media.

It is also possible to prepare catalysts for the present invention by copolymerizing the vinyl ethers of structure III or IV with perfluoroethylene and/or perfluoroalpha-olefins. A preferred copolymer prepared by polymerizing perfluoroethylene with a perfluorovinyl ether containing attached sulfonic acid groups would have the following structure:

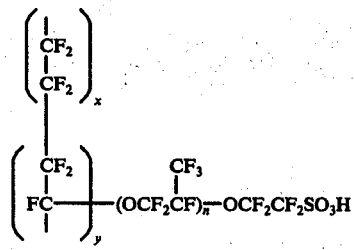

wherein n = 1 or 2 and the ratio of x over y varies from about 2 to about 50. The polymer of structure V is available commercially under the tradename of NAFION ® resin. Catalysts of the above-noted structure V offer the advantages of high concentrations of accessible acid groups in a solid phase.

The catalyst of the present invention is supported on a porous solid inert support. The supported catalysts possess greater activity per unit of acid present than do the unsupported catalysts. By porous solid support is meant an inert support material having a porous structure and an average pore diameter of between about 50 A and about 600 A or higher. Preferably, the average pore diameter of the support is greater than about 200 A. The porous solid support of the subject invention is preferably selected from the inorganic oxide group consisting of alumina, fluorided alumina, zirconia, silica, silica-alumina, magnesia, chromia, boria, and mixtures and combinations thereof. Other porous solid supports may also be used such as bauxite, kieselguhr, kaolin, bentonite, diatomaceous earth and the like. Other porous solid supports such as polytetrafluoroethylene, carbon, e.g., charcoal, polytrichlorofluoroethylene, porous glass, and the like may also be used. Basically, the support should be substantially inert to the catalyst, and be insoluble in the mixture under reaction conditions.

The average pore diameter (also known as effective pore diameter) of the support, which is related to the ratio of pore volume to surface area, is an important consideration in the choice of support. Generally, as the average pore diameter of the support is increased, the activity of the catalyst is increased. For example, as shown in the Illustrative Embodiments which follow, an isomerization catalyst composition having a porous glass support with a 207 A average pore diameter was only about 60% as active as an isomerization catalyst composition having a porous glass support with a 310 A average pore diameter. Most preferably, the support should possess both a high surface area and a high average pore diameter.

The weight ratio of catalyst to support varies from about 0.1:100 to about 30:100, preferably from about 1:100 to about 15:100. The support is preferably impregnated with the catalyst by dissolving the catalyst in a solvent, such as ethanol, mixing the support and the catalyst solution, and then drying the impregnated support under vacuum at a temperature of between about 25° and about 100° C so as to remove the solvent.

B. Isomerization of Normal Alkanes

Heretofore, it has been known that the isomerization of normal paraffins, particularly normal hexane, to their equilibrium mixtures of branched chain isomers, substantially increases the octane rating of the paraffinic hydrocarbons. In attempting to produce such equilibrium mixtures of isoparaffinic hydrocarbons, several catalytic processes have been developed. In one lower temperature process, isomerization is effected over an aluminum chloride catalyst. This process is costly to operate because of extensive corrosion effects caused by the acidic sludge formed from the aluminum chloride catalyst material, thereby requiring expensive alloy equipment. Moreover, moisture and high-molecular weight hydrocarbons usually present as contaminants in the charge stock cause deterioration of the catalyst and necessitate its frequent replacement. One higher temperature process utilizes a catalyst such as platinum on a silica-alumina base to promote hydroisomerization of normal paraffins in the presence of hydrogen at temperatures of the order of 700° to 800° F. At these high temperatures, the equilibrium mixture of isomers is such that substantial recycling of a portion of the paraffin feed is necessary to obtain the desired improvement in octane ratings.

There are numerous other catalyst systems useful in the isomerization of normal paraffins. These catalyst systems include hydrogen mordenite and platinum on alumina, U.S. Pat. No. 3,432,568; hydrofluoric acidantimony pentafluoride, U.S. Pat. No. 3,903,196; zeolites, U.S. Pat. No. 3,770,845; and $SBF_5$—HF on a ruthenium-promoted fluorided alumina, U.S. Pat. No. 3,864,425.

In the present invention, a $C_4$ to $C_8$ normal paraffin feedstock is isomerized by contacting the feed at a temperature of between about 125° and 225° C and a pressure of between about 0 psig and about 1,000 psig with the catalyst composition disclosed herein.

The catalysts of the present invention possess an improved activity, selectivity and stability over many of the known isomerization catalysts. In addition, the present catalysts, contrasting numerous other popular isomerization catalysts, are not extremely sensitive to water contamination. For example, a water concentration of about 100–150 parts per million in a normal hexane feed stream had no effect on a catalyst of the present invention. Further, as compared to a commercial platinum-on-mordenite isomerization catalyst, the catalyst employed in our invention can catalytically promote an isomerization reaction at a significantly lower temperature (75° C lower). At this lower temperature, not only is the conversion of normal paraffins to isoparaffins substantially increased, but the lower temperature also reduces the excess cracking often encountered at the higher temperatures employed with other catalysts.

The paraffin feed which can be isomerized according to the process of the present invention includes substantially pure normal paraffins having from 4 to 8 carbon atoms, mixtures of such normal paraffins, or hydrocarbon fractions rich in such normal paraffins. The paraffin feed may also contain other isomerizable paraffins such as cycloparaffins (sometimes referred to as naphthenes). The most preferred feedstocks to the process of the present invention are a $C_5$ and/or $C_6$ normal paraffin feed. A particularly preferred feedstock is one containing predominantly (greater than 60% volume) normal hexane.

The stability of the present catalysts in isomerizing a normal paraffin feedstock is greatly improved by the addition of certain hydrocarbon catalyst stabilizers such as isobutane and benzene. When employing isobutane as a stabilizer, the volume ratio of isobutane present in the feed to normal paraffin in the feed should be between about 0:5:1 to about 2:1, preferably about 1:1. It has been found that a ratio of isobutane to normal hexane feed of about 1:1 results in a much improved catalyst stability and activity over a feedstock containing no isobutane. Further, it has been found that a 1:1 isobutane to normal hexane ratio gives better results than does either 0.5:1 or 2:1 ratio. When employing benzene as the catalyst stabilizer, the volume ratio of benzene to normal paraffin in the feed should be between about 0.002:1 and about 0.02:1, perferably between about 0.003:1 and about 0.01:1. It has been found that by increasing the benzene concentration in a normal hexane feed from about 0.25% to 0.5%, the activity of the catalyst is increased. A further increase to 1.0% benzene shows no advantage over 0.5% benzene.

Reaction temperature is varied between about 125° C and about 225° C, preferably between about 175° C and about 200° C. The reaction temperature must be kept below about 225° C due to the lack of stability of the catalyst at temperatures of over 250° C. In general, the activity of the catalyst is greater at the higher temperatures. That is, as the temperature increases, the conversion of normal paraffin increases.

In general, the pressure in the isomerization reaction zone is maintained at between about 0 psig and about 500 psig, preferably between about 50 psig and about 100 psig. The reaction may take place in either a gaseous phase or a liquid phase.

The process may be carried out either as a batch or continuous type of operation, although it is preferred to carry out the process continuously. When operated as a batch operation, the present process is characterized by the use of vigorous mechanical stirring or shaking of the reactants and catalyst. When employing a continuous process, the feed streams may be contacted with the catalyst in any suitable reactor. In one embodiment, the catalyst is packed in a vertical, tubular reactor bed with inert supports, such as ceramic balls or silicon carbide, above and below the catalyst to prevent entrainment of the solid catalyst. In a further embodiment, the catalyst is mixed an inert material, such as quartz, and loaded in the reactor so as to improve the fluid dynamics of the system. The flow of the reactant feed stream may be upflow or downflow as desired.

The weight hourly space velocity effectively measures the catalyst concentration employed, and hence also measures the relative activity of the catalyst. Weight hourly space velocity (WHSV) is defined as the weight per hour of normal paraffin in the feed divided by the weight of catalyst (not including support) employed. For a non-supported catalyst, the WHSV varies from between about 0.05 $hr^{-1}$ and about 2.0 $hr^{-1}$, preferably about 0.4 $hr^{-1}$ and about 1.0 $hr^{-1}$. For a supported catalyst, the WHSV varies from between about 0.3 $hr^{-1}$ and about 10.0 $hr^{-1}$, preferably about 1.0 $hr^{-1}$ and about 4.0 $hr^{-1}$. The higher WHSV for the supported catalyst reflects the increased activity of the supported catalyst per unit of catalyst.

Hydrocarbon isomers produced from our process are useful as feedstocks for hydrocarbon alkylation processes. Further, they find utility as a gasoline blending stock because of their high antiknock properties.

The invention is further illustrated by means of the following Comparative Examples and Illustrative Embodiments which are given for the purpose of illustration only, and the invention is not to be regarded as limited to any of the specific materials or conditions recited therein.

In all examples and embodiments, the reactor employed was a 17-inch stainless steel tube equipped with a liquid feed downflow inlet. The catalyst bed occupied the central portion of the reactor, with several grams of carborundum chips on both sides of the catalyst bed to prevent entrainment of the catalyst.

In Comparative Examples I$b$-III$b$ and Illustrative Embodiments I$b$ to X$b$, the hydrocarbon feed comprised normal hexane. The product from the reactor were analyzed by GLC.

Comparative Example I$b$

The catalyst employed in Comparative Examples I$b$ and II$b$ was prepared by grinding Nafion XR granules with a blender to 150 micrometer or less particle size. The ground material was then treated twice with 30% sulfuric acid to convert the material from a potassium ($K^+$) form to the $H^+$ form. The treated material was collected by filtration, washed with distilled water unitl the washings were neutral, and then dried at 100° C and 3 mm pressure for 16 hours. The resulting catalyst contained about 0.85 milliequivalents of acid per gram of catalyst. The structure for the resulting catalyst is exemplified by the following repeating structure where $n = 1$ or 2 and the ratio of $x$ over $y$ varies from between 2 and about 50:

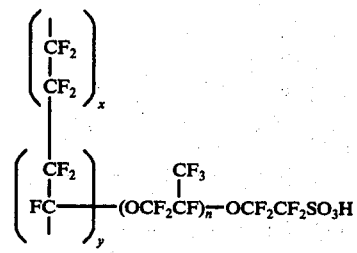

About 2.5 grams of the resulting polymer catalyst was mixed with 7.5 grams of quartz and loaded in the reactor. Reaction conditions were a pressure of 20 psig, weight hourly space velocity (defined as the grams of hydrocarbon feed per hour divided by the grams of catalyst employed) of 0.9 hr$^{-1}$, and a reaction temperature of 175° C. The results are presented below in Table 1b.

Table 1b

| Time, Hr. | 1 | 2 | 3 | 4 | 5 | 6 | 7 |
|---|---|---|---|---|---|---|---|
| Composition of Product, % w | | | | | | | |
| $C_2$-$C_3$ | 3 | 2 | 1 | 0.8 | 0.6 | 0.4 | 0.2 |
| Isobutane | 14 | 11 | 9 | 8 | 5.5 | 3.5 | 2 |
| Isopentane + n-pentane | 22 | 18 | 15 | 13 | 10 | 8 | 5.7 |
| 3-Methylpentane | 8 | 7 | 7 | 5 | 4 | 3 | 1.5 |
| 2-Methylpentane | 13 | 12 | 11 | 9 | 7 | 4.5 | 3 |
| 2,3-Dimethylbutane | 5 | 4 | 4 | 3 | 2.5 | 1.5 | 1 |
| 2,2-Dimethylbutane | 8 | 7 | 6 | 5 | 4 | 2 | 0.5 |
| n-Hexane | 15 | 30 | 40 | 51 | 63 | 74 | 85 |
| $C_7$ Compounds | 10 | 8 | 6 | 4 | 3 | 2 | 1 |
| $\geq C_8$ Compounds | 2 | 1.5 | 1 | 1 | 0.5 | 0.2 | 0.1 |

Comparative Example IIb

Comparative Example IIb was conducted in a similar manner to Comparative Example Ib except that the feed comprised a 1:1 volume ratio of isobutane to n-hexane. The pressure was maintained at 45–50 psig, and the WHSV (n-hexane feed only) at 0.47 hr$^{-1}$. The temperature was raised from 175° to 200° C after 54 hours. The results (on an iC$_4$ free basis) are presented below in Table 2b. After 54 hours, the unit was shut down over a weekend period.

Table 2b

| Time, Hrs. | 6 | 24 | 28 | 32 | 50 | 54 | 62 | 82 |
|---|---|---|---|---|---|---|---|---|
| Temperature, ° C | 175 | 175 | 175 | 175 | 175 | 200 | 200 | 200 |
| Composition of Product, % w (iC$_4$ free basis) | | | | | | | | |
| $C_2$-$C_3$ | 0.5 | 0.3 | 0.3 | 0.3 | 0.3 | 0.3 | 0.3 | 0.3 |
| Isopentane + n-pentane | 1.5 | 0.8 | 0.6 | 0.5 | 0.5 | 0.6 | 0.6 | 0.3 |
| 3-Methylpentane | 15 | 14 | 14 | 13 | 14 | 13 | 12 | 7 |
| 2-Methylpentane | 25 | 25 | 23 | 23 | 22 | 20 | 19 | 12 |
| 2,3-Dimethylbutane | 10 | 10 | 9 | 9 | 9 | 8 | 7 | 4 |
| 2,2-Dimethylbutane | 16 | 15 | 13 | 13 | 13 | 12 | 11 | 3 |
| n-Hexane | 30 | 34 | 39 | 40 | 41 | 45 | 50 | 73 |
| Methylcyclopentane | 0.2 | 0.05 | 0.05 | 0.05 | 0.05 | 0.05 | 0.03 | 0.02 |
| $C_7$ Compounds | 0.7 | 0.3 | 0.3 | 0.25 | 0.2 | 0.25 | 0.2 | 0.1 |
| $\geq C_8$ Compounds | 0.3 | 0.1 | 0.1 | 0.1 | 0.1 | 0.1 | 0.05 | 0.05 |

Illustrative Embodiment Ib

Illustrative Embodiments Ib to Xb disclose the use of the catalyst of the present invention on various supports. In all cases, the supported catalyst was placed in a round-bottomed flask and a 5.5% solution of Nafion XR resin in ethanol was added dropwise. The resulting mixture was vigorously stirred with a mechanical stirrer during the impregnation, and stirring continued for 30 minutes thereafter. The ethanol was removed from the resulting supported catalyst by evaporation on a rotary evaporator at 25° C and 1 mm pressure for 2 hours and at 60° C and 1 mm pressure for an additional 4 hours. The dried, supported catalyst was then ground to a sufficient size so as to pass through a number 60 sieve. The resulting active catalyst structure is the same as that shown in Comparative Example Ib.

In Illustrative Embodiment Ib, the support employed was a high surface area silica having a 1.65 ml/g pore volume, 300 m$^2$/g surface area and a 210 A average pore diameter. Nine grams of the resulting catalyst (6% catalyst on support) were loaded in the reactor. Reaction conditions were 20 psig pressure, 175° C temperature, and a WHSV of 3.0 hr$^{-1}$. Note that in all embodiments and claims, WHSV is measured on a support-free basis. The results are presented below in Table 3b.

Table 3b

| Time, Hrs. | 2 | 4 | 5 | 6 | 6.5 | 7.5 | 8.5 |
|---|---|---|---|---|---|---|---|
| Composition of Product, % w | | | | | | | |
| $C_2$-$C_3$ | 1.5 | 1.5 | 1.0 | 0.6 | 0.6 | 0.4 | 0.2 |
| Isobutane | 8 | 6 | 6 | 4 | 5 | 3 | 2 |
| Isopentane + n-pentane | 12 | 10 | 10 | 7 | 8 | 4 | 2 |
| 3-Methylpentane | 12 | 11 | 10 | 9 | 9 | 7 | 5 |
| 2-Methylpentane | 20 | 18 | 16 | 16 | 15 | 14 | 10 |
| 2,3-Dimethylbutane | 8 | 7 | 6 | 5 | 4 | 4 | 2 |
| 2,2-Dimethylbutane | 12 | 11 | 10 | 7 | 5 | 4 | 1 |
| n-Hexane | 20 | 30 | 37 | 42 | 50 | 62 | 77 |
| Methylcyclopentane | 0.2 | 0.2 | 0.2 | 0.1 | 0.1 | 0.1 | 0.05 |
| $C_7$ Compounds | 6 | 4 | 3 | 2 | 2 | 1 | 0.5 |
| $\geq C_8$ Compounds | 0.5 | 0.4 | 0.3 | 0.3 | 0.3 | 0.2 | 0.1 |

Illustrative Embodiment IIb

An identical catalyst to that employed in Illustrative Embodiment Ib was employed in Illustrative Embodiment IIb. However, in Illustrative Embodiment Ib, the feed stream comprised isobutane and n-hexane in a 1:1 volume ratio. Reaction conditions included a 40–50 psig pressure and a WHSV of 2.2 hr$^{-1}$. The temperature was increased from 175° to 200° C after 124 hours. Note that in all embodiments, WHSV is measured on basis of the n-hexane feed only, i.e., moderators such as isobutane or benzene are not included. The results are presented below in Table 4b.

Table 4b

| Time, Hours | 4 | 28 | 70 | 98 | 124 | 148 | 177 |
|---|---|---|---|---|---|---|---|
| Temperature, ° C | 175 | 175 | 175 | 175 | 175 | 200 | 200 |
| Composition of Product, % w (iC$_4$ free basis) | | | | | | | |
| $C_2$-$C_3$ | 0.5 | 0.3 | 0.3 | 0.3 | 0.2 | 0.5 | 0.2 |

Table 4b-continued

| Time, Hours | 4 | 28 | 70 | 98 | 124 | 148 | 177 |
|---|---|---|---|---|---|---|---|
| Temperature, °C | 175 | 175 | 175 | 175 | 175 | 200 | 200 |
| Isopentane + n-pentane | 2 | 0.6 | 0.5 | 0.4 | 0.4 | 0.6 | 0.3 |
| 3-Methylpentane | 12 | 12 | 12 | 12 | 12 | 13 | 7 |
| 2-Methylpentane | 20 | 20 | 20 | 20 | 20 | 21 | 13 |
| 2,3-Dimethylbutane | 8 | 8 | 8 | 8 | 8 | 8 | 4 |
| 2,2-Dimethylbutane | 12 | 12 | 11 | 12 | 12 | 16 | 4 |
| n-Hexane | 46 | 48 | 49 | 48 | 48 | 39 | 70 |
| Methylcyclopentane | 0.1 | 0.05 | 0.05 | 0.05 | 0.05 | 0.1 | 0.05 |
| $C_7$ Compounds | 0.3 | 0.2 | 0.2 | 0.2 | 0.2 | 0.3 | 0.1 |
| $\geq C_8$ Compounds | 0.1 | 0.1 | 0.05 | 0.05 | 0.05 | 0.1 | — |

Illustrative Embodiment IIIb

Illustrative Embodiment IIIb was conducted in a similar manner to Illustrative Embodiment IIb except that the isobutane to n-hexane ratio was maintained at 0.5:1. Other operating conditions included a pressure of 40 psig, temperature of 175° C and a WHSV of 2.9 hr$^{-1}$. The results are presented below in Table 5b.

Table 5b

| Time, Hrs. | 4 | 22 | 27 | 46 | 51 | 70 |
|---|---|---|---|---|---|---|
| Composition of Product, % w (iC$_4$ free basis) | | | | | | |
| $C_2$-$C_3$ | 0.9 | 0.6 | 0.5 | 0.5 | 0.5 | 0.3 |
| Isopentane | 3 | 1.5 | 1.5 | 1.5 | 1.5 | 1.0 |
| 3-Methylpentane | 8 | 8 | 8 | 7 | 7 | 4 |
| 2-Methylpentane | 13 | 14 | 14 | 13 | 13 | 8 |
| 2,3-Dimethylbutane | 5 | 5 | 5 | 5 | 4 | 3 |
| 2,2-Dimethylbutane | 7 | 7.5 | 6 | 6 | 5 | 1.5 |
| n-Hexane | 62 | 63 | 64 | 66 | 68 | 82 |
| Methylcyclopentane | 0.1 | 0.1 | 0.1 | 0.1 | 0.05 | 0.05 |
| $C_7$ Compounds | 0.4 | 0.4 | 0.4 | 0.4 | 0.3 | 0.2 |
| $\geq C_8$ Compounds | 0.1 | 0.1 | 0.1 | 0.1 | 0.1 | 0.05 |

Illustrative Embodiment IVb

Benzene acts as does isobutane in improving the selectivity and stability of the catalysts of the present invention. In Illustrative Embodiments IVb, an identical catalyst to that employed in Illustrative Embodiments Ib, IIb and IIIb was used. The normal hexane feed, however, contained 0.5% volume benzene and no isobutane. Other reaction conditions included a pressure of 20 psig, WHSV of 2.3 hr$^{-1}$, and a temperature of 175° C. The results are presented below in Table 6b.

Table 6b

| Time, Hrs. | 5 | 21 | 45 | 69 | 77 | 98 |
|---|---|---|---|---|---|---|
| Composition of Product, % w | | | | | | |
| $C_2$-$C_3$ | 0.2 | 0.2 | 0.4 | 0.3 | 0.1 | 0.05 |
| Isobutane | 0.3 | 0.3 | 0.3 | 0.3 | 0.2 | 0.1 |
| Isopentane + n-pentane | 0.4 | 0.4 | 0.3 | 0.3 | 0.3 | 0.1 |
| 3-Methylpentane | 12 | 12 | 12 | 12 | 10 | 4 |
| 2-Methylpentane | 20 | 20 | 20 | 20 | 18 | 8 |
| 2,3-Dimethylbutane | 8 | 8 | 8 | 8 | 7 | 2 |
| 2,2-Dimethylbutane | 11 | 12 | 11 | 12 | 10 | 2 |
| n-Hexane | 48 | 47 | 48 | 47 | 53 | 82 |
| Methylcyclopentane | 0.1 | 0.1 | 0.1 | 0.05 | 0.05 | 0.05 |
| $C_7$ Compounds | 0.2 | 0.2 | 0.2 | 0.2 | 0.2 | 0.05 |
| $\geq C_8$ Compounds | 0.05 | 0.05 | 0.05 | 0.05 | 0.05 | Trace |
| Benzene | 0.3 | 0.4 | 0.45 | 0.4 | 0.45 | 0.45 |

Illustrative Embodiment Vb

Illustrative Embodiment Vb differs from Illustrative Embodiment IVb only in that the pressure was maintained at 18 psig, and the percentage of benzene in the normal hexane feed was reduced to 0.25% volume. The results are presented below in Table 7b.

Table 7b

| Time, Hrs. | 4 | 24 | 46 | 70 | 78 | 97 |
|---|---|---|---|---|---|---|
| Composition of Product, % w | | | | | | |
| $C_2$-$C_3$ | 0.2 | 0.2 | 0.2 | 0.2 | 0.2 | 0.1 |
| Isobutane | 0.5 | 0.5 | 0.5 | 0.5 | 0.5 | 0.3 |
| Isopentane + n-pentane | 0.7 | 0.7 | 0.6 | 0.7 | 0.7 | 0.3 |
| 3-Methylpentane | 10 | 8 | 9 | 8 | 7 | 4 |
| 2-Methylpentane | 17 | 16 | 15 | 15 | 13 | 7 |
| 2,3-Dimethylbutane | 6.5 | 6 | 6 | 6 | 5 | 2 |
| 2,2-Dimethylbutane | 9 | 8 | 8 | 7 | 6 | 1.5 |
| n-Hexane | 56 | 59 | 59 | 62 | 67 | 85 |
| Methylcyclopentane | 0.1 | 0.1 | 0.1 | 0.1 | 0.1 | 0.05 |
| $C_7$ Compounds | 0.3 | 0.3 | 0.3 | 0.3 | 0.3 | 0.2 |
| $\geq C_8$ Compounds | 0.1 | 0.1 | 0.1 | 0.1 | 0.1 | 0.05 |
| Benzene | 0.1 | 0.15 | 0.15 | 0.1 | 0.1 | 0.15 |

Illustrative Embodiment VIb

The only change from Illustrative Embodiment Vb is that in Illustrative Embodiment VIb, the benzene concentration in the n-hexane feed is increased to 1.0% volume. The results are found below in Table 8b.

Table 8b

| Time, Hrs. | 4 | 23 | 28 | 47 | 52 | 71 |
|---|---|---|---|---|---|---|
| Composition of Product, % w | | | | | | |
| $C_2$-$C_3$ | 0.1 | 0.1 | 0.1 | 0.1 | 0.1 | 0.05 |
| Isobutane | 0.2 | 0.2 | 0.2 | 0.2 | 0.2 | 0.1 |
| Isopentane | 0.3 | 0.2 | 0.2 | 0.2 | 0.2 | 0.1 |
| 3-Methylpentane | 9 | 8 | 8 | 8 | 7 | 4 |
| 2-Methylpentane | 15 | 15 | 15 | 14 | 13 | 6 |
| 2,3-Dimethylbutane | 6 | 5 | 5 | 5 | 4.5 | 2 |
| 2,2-Dimethylbutane | 7 | 6 | 6 | 6 | 5 | 1.5 |
| n-Hexane | 61 | 64 | 64 | 65 | 68 | 85 |
| Methylcyclopentane | 0.1 | 0.1 | 0.1 | 0.1 | 0.1 | 0.05 |
| $C_7$ Compounds | 0.1 | 0.1 | 0.1 | 0.1 | 0.1 | 0.1 |
| $\geq C_8$ Compounds | 0.05 | 0.05 | Trace | Trace | Trace | — |
| Benzene | 0.6 | 0.9 | 0.8 | 0.90 | 0.90 | 0.90 |

Illustrative Embodiment VIIb

In Illustrative Embodiment VIIb, the catalyst of the present invention was supported on a silica-alumina base (MSA-3) having a 1.0 ml/g pore volume, 510 m²/g surface area, and an 80 A average pore diameter. About 12 grams of the resulting inpregnated catalyst having a catalyst to support weight ratio of 4.5:100 was loaded in the reactor. Operating conditions included 40 psig pressure, 175° C temperature, WHSV of 2.12 hr⁻¹, and an isobutane to n-hexane feed ratio of 1:1. The results are present below in Table 9b.

Table 9b

| Time, Hrs. | 4 | 20 | 25 | 28 | 44 | 50 |
|---|---|---|---|---|---|---|
| Composition of Product, % w (iC₄ free basis) | | | | | | |
| C₂–C₃ | 1 | 0.4 | 0.2 | 0.2 | 0.3 | 0.2 |
| Isopentane | 2 | 0.5 | 0.4 | 0.4 | 0.3 | 0.12 |
| 3-Methylpentane | 7 | 7 | 7 | 6 | 6 | 5 |
| 2-Methylpentane | 11 | 11 | 10 | 10 | 10 | 8 |
| 2,3-Dimethylbutane | 4 | 4 | 3 | 3 | 3 | 2 |
| 2,2-Dimethylbutane | 4 | 4 | 4 | 3 | 3 | 1.5 |
| n-Hexane | 71 | 73 | 75 | 77 | 77 | 83 |
| Methylcyclopentane | 0.1 | 0.05 | 0.05 | 0.05 | 0.05 | 0.05 |
| C₇ Compounds | 0.3 | 0.2 | 0.2 | 0.2 | 0.2 | 0.11 |
| ≧C₈ Compounds | 0.1 | 0.05 | 0.05 | 0.05 | 0.05 | 0.05 |

Illustrative Embodiment VIIIb

In Illustrative Embodiment VIIIb, the support was a porous glass (98% SiO₂ and 2% B₂O₃) having a pore volume of 1.2 ml/g, surface area of 154 m²/g, and an average pore diameter of 310 A. The impregnated catalyst had a catalyst to support weight ratio of 5:100. About 4.5 grams of the supported catalyst was loaded in the reactor. Reaction conditions were a 40 psig pressure, WHSV of 5.3 hr⁻¹, 175° C temperature, and an isobutane to n-hexane ratio of 1:1. The results are presented below in Table 10b.

Table 10b

| Time, Hrs. | 2 | 23 | 45 | 53 | 77 | 98 |
|---|---|---|---|---|---|---|
| Composition of Product, % w (iC₄ free basis) | | | | | | |
| C₂–C₃ | 0.3 | 0.3 | 0.4 | 0.4 | 0.3 | 0.3 |
| Isopentane + n-pentane | 3.0 | 1.0 | 1.1 | 1.0 | 0.9 | 0.9 |
| 3-Methylpentane | 15 | 15 | 15 | 14.5 | 15 | 14.5 |
| 2-Methylpentane | 25 | 25 | 25 | 25 | 25 | 25 |
| 2,3-Dimethylbutane | 10 | 10 | 10 | 9.5 | 10 | 9.5 |
| 2,2-Dimethylbutane | 16 | 16 | 16 | 16 | 15 | 15 |
| n-Hexane | 30 | 32 | 32 | 33 | 33 | 34 |
| Methylcyclopentane | 0.1 | 0.1 | 0.1 | 0.1 | 0.1 | 0.1 |
| C₇ Compounds | 0.5 | 0.3 | 0.3 | 0.3 | 0.3 | 0.3 |
| ≧C₈ Compounds | 0.2 | 0.1 | 0.1 | 0.1 | 0.1 | 0.1 |

Illustrative Embodiment IXb

In Illustrative Embodiment IXb, the support employed was a porous glass having a pore volume of 1.5 ml/g, surface area of 292 m²/g, and an average pore diameter of 207 A. The catalyst to support ratio was 4.5:100, and 4.5 grams of supported catalyst were employed. Reaction conditions included 40 psig pressure, WHSV of 4.4 hr⁻¹, temperature of 175° C, and an isobutane to n-hexane ration of 1:1. The results are presented below in Table 11b.

Table 11b

| Time, Hrs. | 2 | 21 | 26 | 47 | 53 | 74 |
|---|---|---|---|---|---|---|
| Composition of Product, % w (iC₄ free basis) | | | | | | |
| C₂–C₃ | 0.3 | 0.3 | 0.3 | 0.2 | 0.2 | 0.2 |
| Isopentane + n-pentane | 2.0 | 0.6 | 0.6 | 0.6 | 0.6 | 0.6 |
| 3-Methylpentane | 12 | 12 | 12 | 12 | 12 | 12 |
| 2-Methylpentane | 20 | 20 | 20 | 20 | 20 | 20 |
| 2,3-Dimethylbutane | 8 | 8 | 8 | 8 | 8 | 7 |
| 2,2-Dimethylbutane | 12 | 12 | 11 | 11 | 12 | 11 |
| n-Hexane | 45 | 47 | 48 | 48 | 47 | 49 |
| Methylcyclopentane | 0.1 | 0.1 | 0.1 | 0.1 | 0.1 | 0.1 |
| C₇ Compounds | 0.4 | 0.3 | 0.3 | 0.3 | 0.3 | 0.3 |
| ≧C₈ Compounds | 0.1 | 0.1 | 0.1 | 0.1 | 0.1 | 0.1 |

Illustrative Embodiment Xb

In Illustrative Embodiment Xb, the support employed was a Pechiney alumina having a pore volume of 0.55 ml/g, surface area of 60 m²/g, and an effective pore diameter of 370 A. Catalyst to support ratio was 2.8:100. About 12 grams of the supported catalyst were loaded in the reactor. Reaction conditions included a 40 psig pressure, 175° C temperature, WHSV of 3.5 hr⁻¹, and an isobutane to n-hexane feed ratio of 1:1. The results are presented below in Table 12b.

Table 12b

| Time, Hrs. | 5 | 26 | 50 | 71 | 77 | 96 |
|---|---|---|---|---|---|---|
| Composition of Product, % w (iC₄ free basis) | | | | | | |
| C₂–C₃ | 0.3 | 0.3 | 0.2 | 0.2 | 0.2 | 108 0.2 |
| Isopentane | 1.0 | 0.8 | 0.8 | 0.8 | 0.8 | 0.5 |
| 3-Methylpentane | 15 | 15 | 15 | 15 | 15 | 10 |
| 2-Methylpentane | 25 | 25 | 25 | 24.5 | 25 | 17 |
| 2,3-Dimethylbutane | 10 | 10 | 10 | 9.5 | 9.5 | 6.5 |
| 2,2-Dimethylbutane | 15 | 15 | 15 | 14.5 | 14.5 | 9 |
| n-Hexane | 33 | 33 | 33 | 34.5 | 34.5 | 56.5 |
| Methylcyclopentane | 0.1 | 0.1 | 0.1 | 0.1 | 0.1 | 0.1 |
| C₇ Compounds | 0.3 | 0.3 | 0.3 | 0.3 | 0.3 | 0.2 |
| ≧C₈ Compounds | 0.1 | 0.1 | 0.1 | 0.1 | 0.1 | 0.05 |

Illustrative Embodiment XIb

In Illustrative Embodiment XIb, the support was a low pore diameter CCI alumina having a pore volume of 0.85 ml/g, a surface area of 250 m²/g, and an effective pore diameter of 136 A. Catalyst to support ratio was about 3.7:100, and about 15 grams of supported catalyst were loaded in the reactor. Reaction conditions include a pressure of 40 psig, temperature of 175° C, WHSV of 2.2 hr⁻¹, and an isobutane to n-hexane raito of 1:1. The results are presented below in Table 13b.

Table 13b

| Time, Hrs. | 2 | 23 | 44 | 66 | 74 | 95 | 100 |
|---|---|---|---|---|---|---|---|
| Composition of Product, % w (C₄ free basis) | | | | | | | |
| $C_2$-$C_3$ | 0.5 | 0.2 | 0.2 | 0.2 | 0.3 | 0.1 | 0.1 |
| Isopentane | 3 | 0.4 | 0.4 | 0.4 | 0.5 | 0.2 | 0.2 |
| 3-Methylpentane | 13 | 12 | 12 | 12 | 12 | 4 | 2 |
| 2-Methylpentane | 21 | 20 | 20 | 20 | 20 | 8 | 4 |
| 2,3-Dimethylbutane | 8 | 8 | 8 | 8 | 8 | 2 | 1 |
| 2,2-Dimethylbutane | 13 | 12 | 12 | 12 | 12 | 2 | 1 |
| n-Hexane | 40 | 48 | 48 | 48 | 48 | 83 | 91 |
| Methylcyclopentane | 0.1 | 0.1 | 0.05 | 0.05 | 0.05 | 0.05 | 0.05 |
| $C_7$ Compounds | 0.3 | 0.2 | 0.2 | 0.2 | 0.2 | 0.1 | 0.1 |
| ≧ $C_8$ Compounds | 0.1 | 0.05 | 0.05 | 0.05 | 0.05 | Trace | — |

Comparative Example IIIb

Comparative Example IIIb was run with an identical catalyst and loading as that employed in Comparative Example IIb. However, in Comparative Example IIIb, the feed comprised n-pentane instead of n-hexane. Other operating conditions included a 45 psig pressure, WHSV of 0.45 hr⁻¹, and an isobutane to n-pentane ratio of 1:1. The temperature was increased from 175° to 200° C after 30 hours. Results are presented below in Table 14b.

Table 14b

| Time, Hrs. | 5 | 26 | 32 | 52 | 60 | 82 | 84 |
|---|---|---|---|---|---|---|---|
| Temperature, ° C | 175 | 175 | 200 | 200 | 200 | 200 | 200 |
| Composition of Product, % w (iC₄ free basis) | | | | | | | |
| $C_2$-$C_3$ | 0.2 | 0.2 | 0.2 | 0.2 | 0.2 | 0.1 | 0.1 |
| Isopentane | 25 | 25 | 30 | 32 | 30 | 15 | 12 |
| n-pentane | 75 | 75 | 70 | 68 | 70 | 85 | 88 |
| $C_6$ Compounds | 0.1 | 0.2 | 0.2 | 0.2 | 0.2 | 0.1 | 0.1 |
| ≧ $C_7$ Compounds | 0.05 | 0.05 | 0.5 | 0.05 | 0.05 | 0.05 | 0.05 |

What is claimed is:

1. An isomerization process which comprises contacting a C₄ to C₈ normal paraffin feedstock at a reaction temperature of between about 125° and about 225° C in the presence of a catalyst composition comprising a solid, perfluorinated polymer catalyst supported on an inert porous carrier having an average pore diameter of between about 50 A and about 600 A in a weight ratio of catalyst to support of between about 0.1:100 and about 20:100 wherein said catalyst contains a repeating structure selected from the group of:

a)
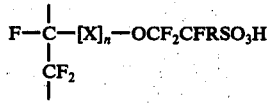

or b)
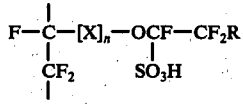

where n is 0, 1 or 2; R is a radical selected from the group consisting of fluorine and perfluoroalkyl radicals having from 1 to 10 carbon atoms; and X is selected from the group consisting of:

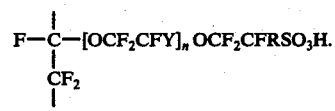

where m is an integer from 2 to 10 and Y is a radical selected from the class consisting of fluorine and the trifluoromethyl radical.

2. A process according to claim 6 wherein said catalyst contains the repeating structure:

$$F-\underset{\underset{CF_2}{|}}{\overset{|}{C}}-[OCF_2CFY]_n OCF_2CFRSO_3H.$$

3. A process according to claim 1 wherein a catalyst stabilizer selected from the group consisting of isobutane and benzene is employed.

4. A process according to claim 3 wherein the catalyst stabilizer is isobutane and wherein the volume ratio of isobutane to normal paraffin in the feedstock is between about 0.5:1 and about 2:1.

5. A process according to claim 3 wherein the catalyst stabilizer is benzene and wherein the volume ratio of benzene to normal paraffin in the feedstock is between about 0.002:1 to about 0.02:1.

6. A process according to claim 4 wherein said normal paraffin feedstock comprises predominantly normal hexane.

7. A process according to claim 4 wherein said catalyst contains the repeating structure:

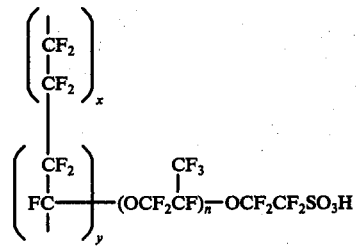

where n is 0, 1 or 2 and the ratio of x over y varies from 2 to about 50.

8. A process to claim 1 wherein said carrier is selected from the group consisting of alumina, silica, silica-alumina, and porous glass.

* * * * *